United States Patent
Takagi et al.

(10) Patent No.: US 11,215,537 B2
(45) Date of Patent: Jan. 4, 2022

(54) INSPECTION APPARATUS AND INSPECTION SYSTEM

(71) Applicant: HORIBA, Ltd., Kyoto (JP)

(72) Inventors: Ikue Takagi, Kyoto (JP); Takashi Matsuyama, Kyoto (JP)

(73) Assignee: HORIBA, LTD., Kyoto (JP)

( * ) Notice: Subject to any disclaimer, the term of this patent is extended or adjusted under 35 U.S.C. 154(b) by 171 days.

(21) Appl. No.: 16/144,673

(22) Filed: Sep. 27, 2018

(65) Prior Publication Data

US 2019/0187030 A1 Jun. 20, 2019

(30) Foreign Application Priority Data

Dec. 15, 2017 (JP) .............................. JP2017-240826

(51) Int. Cl.
*G01M 15/10* (2006.01)
*G01N 1/22* (2006.01)
(Continued)

(52) U.S. Cl.
CPC ........... *G01N 1/2252* (2013.01); *F01M 11/12* (2013.01); *G01M 15/102* (2013.01);
(Continued)

(58) Field of Classification Search
CPC .. G01N 1/2252; G01N 33/287; G01N 23/223; G01N 2015/03; G01N 2015/0046;
(Continued)

(56) References Cited

U.S. PATENT DOCUMENTS 2,957,986 A * 10/1960 Quigg ..................... G01F 9/001
250/303
2010/0122571 A1* 5/2010 Han ........................ G01N 11/06
73/54.01
(Continued)

FOREIGN PATENT DOCUMENTS

| CN | 104154963 A | 11/2014 |
| CN | 104655215 A | 5/2015 |

(Continued)

OTHER PUBLICATIONS

EESR dated Mar. 28, 2019 issued for European Patent Application No. 18 196 915.5, 14 pgs.
(Continued)

*Primary Examiner* — Lisa M Caputo
*Assistant Examiner* — Alex T Devito
(74) *Attorney, Agent, or Firm* — Brooks Kushman P.C.

(57) ABSTRACT

To measure an internal state of an engine, for example, the engine oil consumption conveniently and correctly, an inspection apparatus of the present invention for inspecting the internal state of the engine by using an exhaust gas of the engine including engine oil includes a data storage unit that stores content information about a plurality of elements contained in the engine oil, a data acceptance unit that accepts analysis information about a plurality of elements contained in the exhaust gas, and an inspection unit that compares the content information about the engine oil with the analysis information to inspect the internal state of the engine.

7 Claims, 5 Drawing Sheets

(51) Int. Cl.
  *G01N 33/28* (2006.01)
  *G01N 23/223* (2006.01)
  *F01M 11/12* (2006.01)
  *G01N 15/06* (2006.01)
  *G01N 21/64* (2006.01)
  *G01N 15/00* (2006.01)

(52) U.S. Cl.
  CPC ......... *G01N 23/223* (2013.01); *G01N 33/287* (2013.01); *G01N 15/0618* (2013.01); *G01N 21/643* (2013.01); *G01N 2015/0046* (2013.01); *G01N 2015/03* (2013.01)

(58) Field of Classification Search
  CPC ............ G01N 15/0618; G01N 21/643; G01N 33/2888; G01M 15/102; F01M 11/12; F01M 2250/60
  See application file for complete search history.

(56) References Cited

U.S. PATENT DOCUMENTS

| | | | |
|---|---|---|---|
| 2011/0170102 A1 | 7/2011 | Janssen et al. | |
| 2014/0060008 A1 | 3/2014 | Dittler et al. | |
| 2017/0081997 A1* | 3/2017 | Potyrailo | G01N 27/026 |

FOREIGN PATENT DOCUMENTS

| | | |
|---|---|---|
| CN | 105675457 A | 6/2016 |
| CN | 105806627 A | 7/2016 |
| JP | 53-088429 A | 8/1978 |
| JP | 57-090134 A | 6/1982 |
| JP | 60-198433 A | 10/1985 |
| JP | 01-239441 A | 9/1989 |
| JP | 2011-247153 A | 12/2011 |
| JP | 2012-092812 A | 5/2012 |
| JP | 2014-016251 A | 1/2014 |
| JP | 2014-055890 A | 3/2014 |

OTHER PUBLICATIONS

Office Action dated Oct. 8, 2020 issued far Japanese Patent Application No. 2017-240826, 9 pgs.
Office Action dated Nov. 17, 2021 issued in Chinese patent application No. 201811113731.1.
Zhou Shengdong et al., "Exploration and Application of Equipment Wear Diagnosis in Metallurgical Industry", Metallurgical Equipment, Jul. 31, 2017, No. 236, pp. 45-48.
Sun Liwei et al., "Diesel Vehicle Fuel Consumption Calculating Model Based on Carbon Balance Method", Small Internal Combustion Engine and Motorcycle, Apr. 28, 2010, vol. 39, No. 2, pp. 68-69.

* cited by examiner

INSPECTION APPARATUS AND INSPECTION SYSTEM

CROSS-REFERENCE TO RELATED APPLICATION

This application claims priority to Japanese Application No. 2017-240826, filed Dec. 15, 2017, the disclosure of which is incorporated in its entirety by reference herein.

TECHNICAL FIELD

The present invention relates to an inspection apparatus, an inspection method, and an inspection system that inspect an internal state of an engine including engine oil.

BACKGROUND ART

Reduction of engine oil negatively affects the quality of automobiles, for example, the lighting of an engine alarm lamp and the wearing of an oil pump. Conventionally, the engine oil consumption has been often found based on a change in the mass of an oil tank before and after the operation of the engine (gravimetric method).

Alternatively, it has been attempted to readily measure the engine oil consumption from exhaust gas without using the gravimetric method. For example, according to a sulfur trace method, a sulfur ingredient contained in the engine oil is detected from the exhaust gas to calculate oil consumption.

According to another method as disclosed in Patent Literature 1, a fluorescent X-ray analyzing instrument analyzes a specific element (specifically, a sulfur ingredient or a chloride ingredient) in the exhaust gas collected by a reagent impregnated filter to measure the engine oil consumption.

However, since the amount of sulfur ingredient in the engine oil has recently decreased, it becomes difficult to correctly distinguish the sulfur ingredient in a fuel from the sulfur ingredient in the engine oil. Thus, the sulfur ingredient is inadequate for a parameter for measuring the oil consumption. Therefore, the engine oil consumption cannot be correctly measured by measuring only the sulfur ingredient.

Alternatively, ingredients in the exhaust gas discharged from burnt engine oil may be measured to inspect the internal state of the engine. However, like the engine oil consumption, the internal state of the engine cannot be correctly inspected by measuring any single ingredient.

CITATION LIST

Patent Literature

[Patent Literature 1] Japanese Unexamined Patent Application Publication No. 1989-239441

SUMMARY OF INVENTION

Technical Problem

Thus, the present invention is devised to solve the above-mentioned problems, and its object is to correctly inspect the engine oil consumption and the internal state of the engine.

Solution to Problem

An engine oil consumption measurement apparatus according to the present invention is an inspection apparatus for inspecting an internal state of an engine including engine oil by using an exhaust gas of the engine, and the inspection apparatus includes a data storage unit that stores content information about a plurality of elements contained in the engine oil, a data acceptance unit that accepts analysis information about a plurality of elements contained in the exhaust gas, and an inspection unit that compares the content information about the engine oil with the analysis information to inspect the internal state of the engine.

An inspection method according to the present invention is an inspection method for inspecting an internal state of an engine including engine oil by using an exhaust gas of the engine, and the inspection method includes acquiring content information about a plurality of elements contained in the engine oil, acquiring analysis information about a plurality of elements contained in the exhaust gas, and comparing the content information with the analysis information to inspect the internal state of the engine.

For example, as compared with the method of measuring a sulfur ingredient for inspection, the method of the present invention of comparing the plurality of elements contained in the engine oil with the plurality of elements contained in the exhaust gas can inspect the internal state of the engine more correctly. Examples of the internal state of the engine include the engine oil consumption and the wearing of components of the engine.

Specifically, the inspection unit desirably calculates the engine oil consumption as the internal state of the engine. According to the present invention, the engine oil consumption can be correctly measured based on the plurality of elements in the engine oil. For example, the inspection unit uses analysis results of sulfur S as conventional, as well as a plurality of elements including phosphorous P, calcium Ca, zinc Zn, and molybdenum Mo in the engine oil. Thus, as compared to the conventional engine oil consumption measurement apparatus using a single ingredient such as sulfur, the engine oil consumption measurement apparatus of the present invention can measure the engine oil consumption more correctly.

The elements contained in the exhaust gas may include elements derived from the fuel for the engine and elements caused by the wearing of the engine, in addition to the elements caused by consumption of the engine oil. For this reason, the inspection unit compares ratios of the plurality of elements in the engine oil with ratios of the plurality of elements in the exhaust gas, and calculates the engine oil consumption using the element having a difference between the both ratios within a predetermined range. This can measure the engine oil consumption more correctly.

To reduce a measurement error due to the fuel for the engine, the data storage unit may further store content information about a plurality of elements contained in the fuel for the engine, and the inspection unit may compare the content information about the engine oil and the content information about the fuel with the analysis information acquired by the element analysis unit to calculate the engine oil consumption.

As described above, the elements contained in the exhaust gas may include elements caused by the wearing of the engine, in addition to the elements caused by the consumption of the engine oil. At this time, wear powders generated by the wearing in the engine are easily dissolved in the engine oil, and when the engine oil is consumed by burning and the like, the wear powders are discharged together with the exhaust gas. Since the content information about the elements contained in the engine oil is known, the elements caused by wearing of the engine can be identified by analyzing the elements in the exhaust gas. Accordingly, the inspection unit can also inspect the wearing of the engine.

Specifically, the inspection unit desirably compares the ratios of the plurality of elements in the engine oil with the ratios of the plurality of elements in the exhaust gas, and detects the element having a difference between the both ratios out of the predetermined range as a wear element generated by wearing.

The different components of the engine have different compositions and thus, the wear element caused by wearing of the engine varies. To identify a wear position of the engine by utilizing this, the data storage unit may further store usage information about a plurality of elements in each component of the engine, and the inspection unit may identify the wear position in the engine based on the usage information and the wear element.

An inspection system using the above-mentioned inspection apparatus includes a filter that collects ingredients contained in an exhaust gas of an engine, an element analysis apparatus that analyzes elements in the ingredients collected by the filter, and the inspection apparatus according to any one of claims 1 to 7. The data acceptance unit accepts analysis information acquired by the element analysis apparatus, and the inspection unit inspects the internal state of the engine using the analysis information acquired by the element analysis apparatus.

Advantageous Effects of Invention

According to the present invention described above, the plurality of elements contained in the engine oil can be compared with the plurality of elements contained in the exhaust gas to correctly inspect the internal state of the engine.

DESCRIPTION OF EMBODIMENTS

First Embodiment

Figure 1:
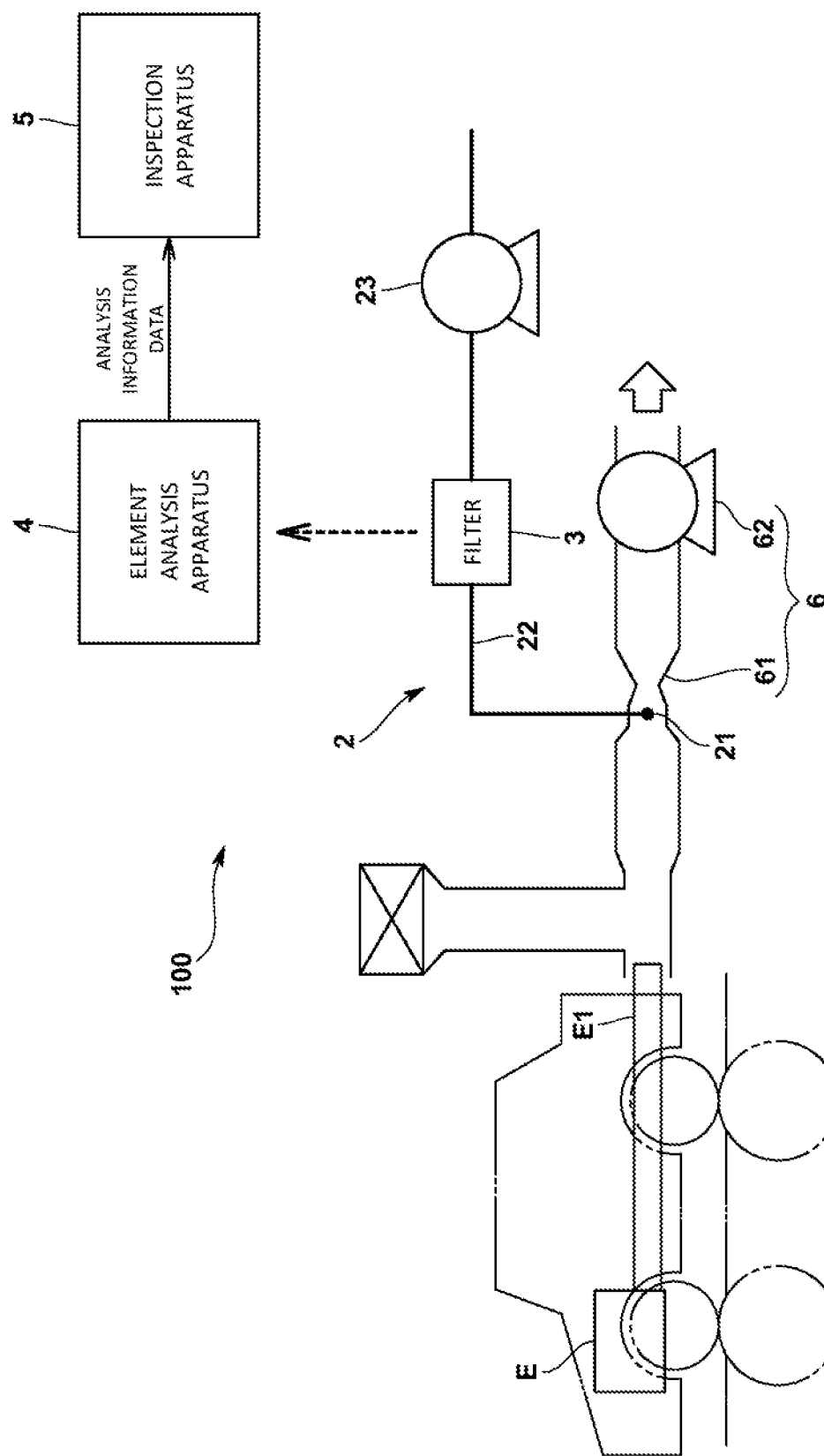
FIG. 1 is a schematic diagram illustrating an entire exhaust gas analysis system according to a first embodiment.
Figure 2:
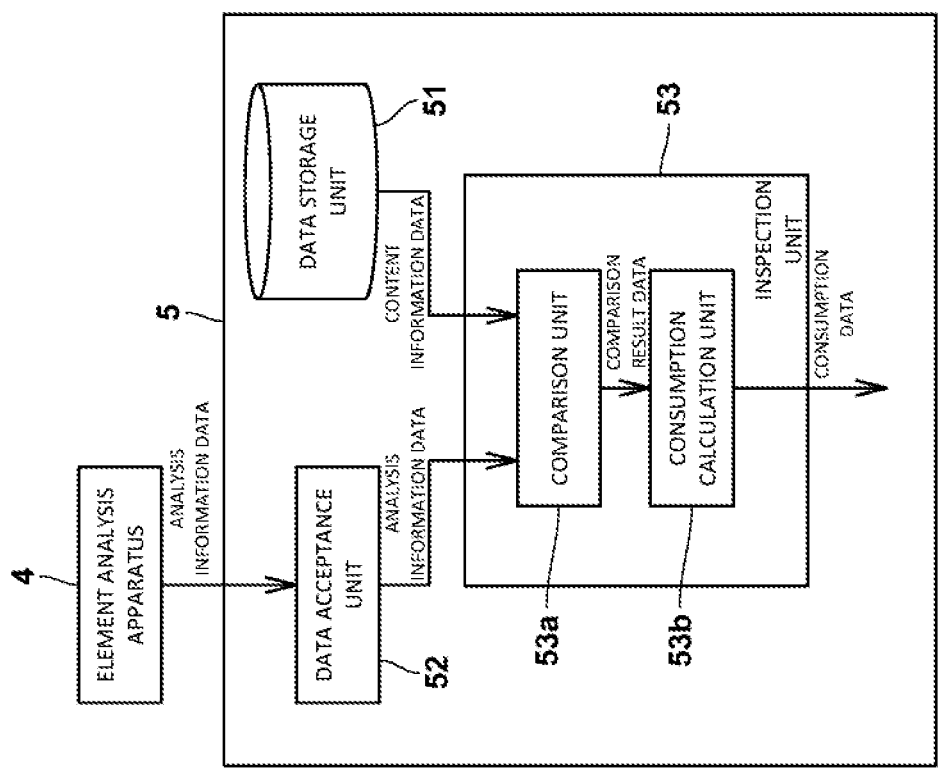
FIG. 2 is a schematic diagram illustrating a functional configuration of an inspection apparatus according to the first embodiment.
Figure 3:
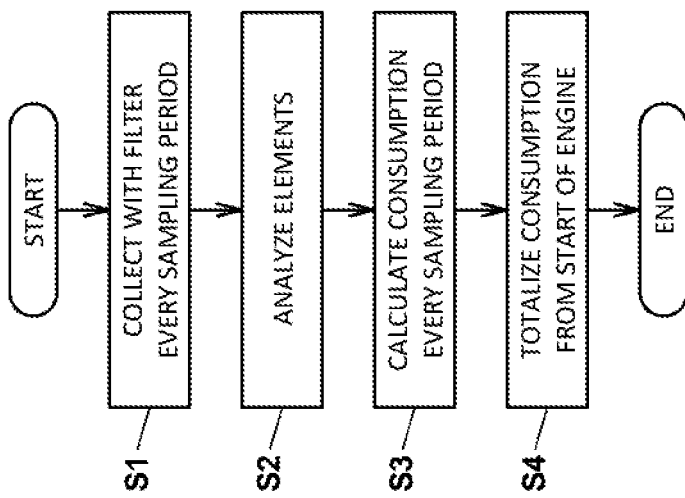
FIG. 3 is a flow chart of an inspection method according to the first embodiment.

An inspection system according to a first embodiment of the present invention will be described below with reference to figures.

An inspection system 100 according to the present embodiment inspects an internal state of an engine E by analyzing elements contained in an exhaust gas discharged from the engine E. In a following example, the inspection system 100 analyzes the elements contained in the exhaust gas to measure engine oil consumption in the engine E. The engine E may be connected alone to an engine dynamo to receive a load, may be mounted in a vehicle travelling on a chassis dynamometer, or may be mounted in a vehicle travelling on an actual road. The engine is used in vehicles, ships, and airplanes, and may be an internal combustion engine or an external combustion engine. The engine oil may be also described as lubricating oil.

Specifically, the inspection system 100 includes a sampling apparatus 2 that samples a part or whole of exhaust gas flowing in an exhaust pipe E1 connected to the engine E, a filter 3 that is provided in the sampling apparatus 2 and collects ingredients (here, PM particles) contained in the exhaust gas, an element analysis apparatus 4 that analyzes elements in the PM particles collected by the filter 3, and an inspection apparatus 5 that measures the engine oil consumption using analysis results of the element analysis apparatus 4.

The sampling apparatus 2 has a sampling port 21 that samples the exhaust gas flowing in the exhaust pipe E1, an exhaust gas channel 22 connected to the sampling port 21, and a suction pump 23 that is provided in the exhaust gas channel 22 and sucks the exhaust gas from the sampling port 21. In the exhaust gas channel 22, a filter attachment unit, to which the filter 3 is exchangeably attached, is provided between the sampling port 21 and the suction pump 23. The exhaust gas channel 22 may be provided with a dehumidifier (cooler), and may be provided with, in place of the dehumidifier, a heater for suppressing condensation of ingredients of the exhaust gas. According to the present embodiment, as shown in FIG. 1, the sampling apparatus 2 is configured such that a constant volume sampling apparatus 6 (CVS) having a constant flow device 61 such as a critical flow venturi and a suction pump 62 dilutes exhaust gas from the exhaust pipe E1 with a dilution gas such as air.

The filter 3 serves to collect PM particles in the exhaust gas, and may be an individually separated batch-type or a rolling-type using a feed roll and a winding roll. Examples of the material for the filter include PTFE coating glass fiber and PTFE.

The element analysis apparatus 4 is a fluorescent X-ray analyzing instrument that irradiates a sample with an X ray and detects an occurred fluorescent X-ray to perform element analysis. The sample is a filter 3 that collects PM particles. The element analysis apparatus 4 according to the present embodiment can perform quantitative analysis the concentration (for example, the mass concentration or the element concentration) or the mass of the elements collected by the filter 3. In the case of the filter 3 of batch type, the filter 3 is detached from the sampling apparatus 2 and set to the element analysis apparatus 4 for quantitative analysis. In the case of the filter 3 of winding type, the element analysis apparatus 4 is installed near the filter 3, and performs quantitative analysis without detaching the filter 3 from the sampling apparatus 2. In this case, the filter 3 of winding type and the element analysis apparatus 4 may be united into an apparatus (element analysis apparatus with filter).

The inspection apparatus 5 acquires data indicating analysis results from the element analysis apparatus 4 to measure the engine oil consumption. The inspection apparatus 5 is a dedicated or general-purpose computer including a CPU, an internal memory, an input/output interface, and an AD converter. The CPU and other components in the inspection apparatus 5 cooperate based on an inspection program stored in the internal memory, thereby performing functions of a data storage unit 51, a data acceptance unit 52, and an inspection unit 53 (a comparison unit 53a and a consumption calculation unit 53b). Each of the units will be described below.

The data storage unit 51 stores content information about a plurality of elements contained in the engine oil. The content information is digital data, and may include the known concentration (for example, the mass concentration) of the plurality of elements contained in the engine oil as well as the composition ratios of the plurality of elements. The content information may be previously inputted by the user, or may be transmitted from the server via the Internet.

The data acceptance unit 52 accepts analysis information acquired by the element analysis apparatus 4. The analysis information is digital data, and may include measured concentration (for example, the mass concentration or the element concentration) of the plurality of elements contained in the engine oil as well as the composition ratios of the plurality of elements. Then, the data acceptance unit 52 transmits the accepted analysis information to the inspection unit 53.

The inspection unit 53 compares the analysis information accepted by the data acceptance unit 52 with the content information stored in the data storage unit 51 to measure the engine oil consumption, in particular, functions as the comparison unit 53a and the consumption calculation unit 53b.

The comparison unit 53a acquires the analysis information and the content information, and compares the ratios (proportions) of the plurality of elements in the engine oil with the ratios (proportions) of the plurality of elements in the exhaust gas. Then, the comparison unit 53a identifies the element having a difference between the both ratios (proportions) within a predetermined range. The predetermined range described herein is the range that can appropriately identify the ratios of the plurality of elements in the engine oil.

For example, it is assumed that the ratios of the plurality of elements in the engine oil is P:1, S:2, Ca:1, Ze:5, and Mo:1. In this case, when the ratios of the plurality of elements in the exhaust gas are P:1, S:2, Ca:5, Ze:5, and Mo:1, the comparison unit 53a identifies P, S, Ze, and Mo as the elements within the predetermined range. In other words, the comparison unit 53a identifies Ca as an element outside the predetermined range. At this time, Ca is derived from the engine oil and any other source. Threshold values for determining whether each element falls within the predetermined range are, for example, values acquired by increasing and decreasing a predetermined proportion (for example, 50%) to and from the ratio of the element in the content information.

The consumption calculation unit 53b calculates the engine oil consumption using the mass concentration of the elements identified as being within the predetermined range by the comparison unit 53a (in the above-described example, P, S, Ze, and Mo).

For example, the consumption calculation unit 53b calculates the engine oil consumption from the measured mass of the elements collected by the filter 3 and the mass concentration of the elements in the content information. The measured mass of the elements is measured by the element analysis apparatus 4. At this time, the consumption calculation unit 53b calculates the engine oil consumption for each of the ingredients as described above, and averages the engine oil consumptions acquired for the plurality of elements to output the engine oil consumption. The calculated engine oil consumption is outputted to output means such as a display. Alternatively, the consumption calculation unit 53b may calculate the mass of the elements collected by the filter 3 from the mass of the PM particles collected by the filter 3 and the mass concentration of the elements. The mass of the PM particles collected by the filter 3 may be found by subtracting the mass of the filter 3 before collection from the mass of the filter 3 after collection. The inspection system 100 may include a collected amount measurement unit for measuring the mass (collected amount) of the PM particles collected by the filter 3, and the consumption calculation unit 53b may use the collected amount measured by the collected amount measurement unit. The collected amount measurement unit has ß-ray source for irradiating the collected PM particles with ß-rays, and a ß-ray detector for detecting the ß-rays that pass through the PM particles. The collected amount measurement unit finds the collected amount of the PM particles, based on the intensity of the ß-ray detected by the ß-ray detector.

Next, an engine oil consumption measuring method using the inspection system 100 will be described.

Every predetermined sampling period from the start of the engine E, the exhaust gas is passed through each filter 3 to collect the PM particles (Step S1). Specifically, the filter 3 is changed every sampling period, and the exhaust gas is passed through the filter such that the exhaust gas is passed through the first filter 3 in a first sampling period, and the exhaust gas is passed through the second filter 3 in a next second sampling period. Then, after collection, the elements in the PM particles collected on the filter 3 are analyzed by using the element analysis apparatus 4 (Step S2). The analysis information acquired by the element analysis apparatus 4 for each filter 3 is transmitted to the inspection apparatus 5.

Figure 4:
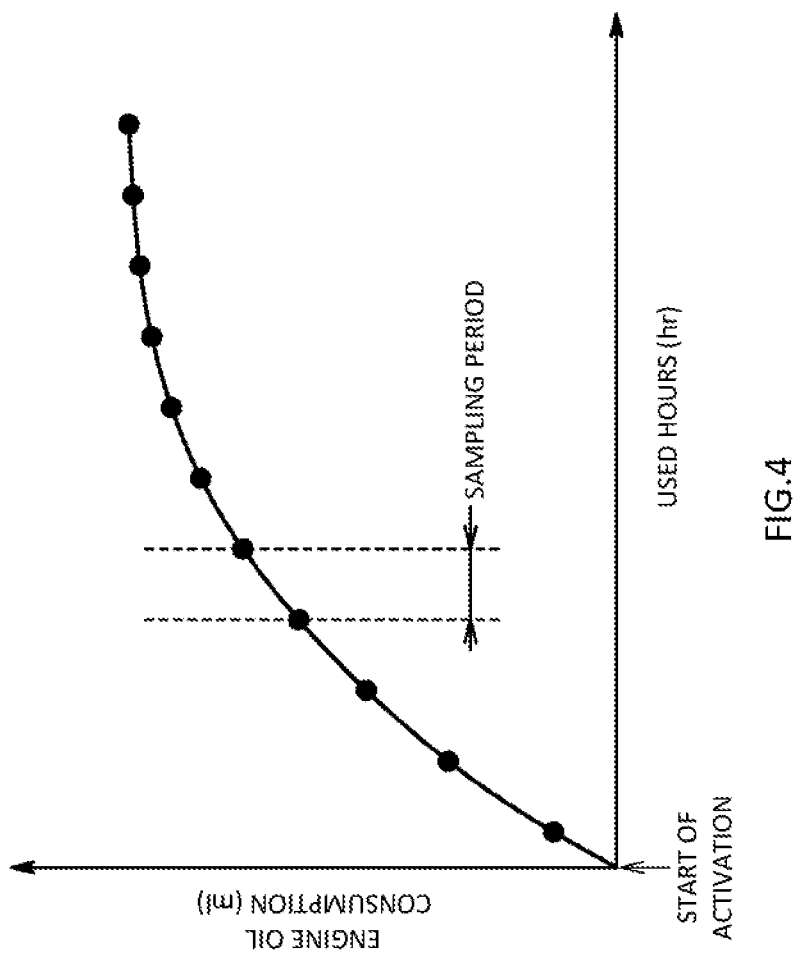
FIG. 4 is a graph illustrating changes in measured values of the engine oil consumption with time according to the first embodiment.

Then, the inspection apparatus 5 compares the analysis information for each filter 3 with the content information about the engine oil to calculate the engine oil consumption in the period of the collection of the particles by each filter 3 (Step S3). By calculating the engine oil consumption in each period and totalizing them, the inspection apparatus 5 can find changes in the engine oil consumption with time from the start of the engine, as shown in FIG. 4 (Step S4).

Alternatively, the engine oil consumption may be calculated by calculating the discharged mass of the plurality of elements, in place of the engine oil consumption, in the period of collection of the particles by each filter 3, and totalizing the discharged mass.

Advantageous Effect of First Embodiment

The engine oil consumption measurement apparatus 100 according to the first embodiment compares the plurality of elements in the engine oil with the plurality of elements in the exhaust gas. Therefore, for example, as compared to the case of measuring only the sulfur ingredient for the inspection, the engine oil consumption can be inspected more correctly.

In the case where the engine oil consumption is mapped when each output torque and each number of revolutions of the engine E vary (for example, horizontal axis (row): number of revolutions, vertical axis (column): output torque), the engine oil consumption measurement apparatus 100 can reduce a time required to find each value (engine oil consumption) on a map. For example, by decreasing the period in which the exhaust gas is passed through the filter 3 to collect the PM particles (for example, one hour), and multiplying the engine oil consumption acquired by measuring the filter 3 by predetermined times (for example, 10 times), the same result as the result acquired by measuring for the predetermined period can be obtained. As a result, the time required to map the engine oil consumption can be reduced.

Second Embodiment

Next, an inspection system according to a second embodiment of the present invention will be described below with reference to figures.

The inspection system 100 according to the present embodiment can also identify a wear position within the engine E by analyzing elements in the exhaust gas. Thus, the present embodiment is different from the first embodiment in a configuration of the inspection apparatus 5.

Wear powders generated due to a wear within the engine E are easily dissolved in the engine oil. When the engine oil is consumed by burning or the like, the wear powders are also burnt and discharged together with the exhaust gas. According to the present embodiment, the wear position within the engine E is identified utilizing this phenomenon.

Figure 5:
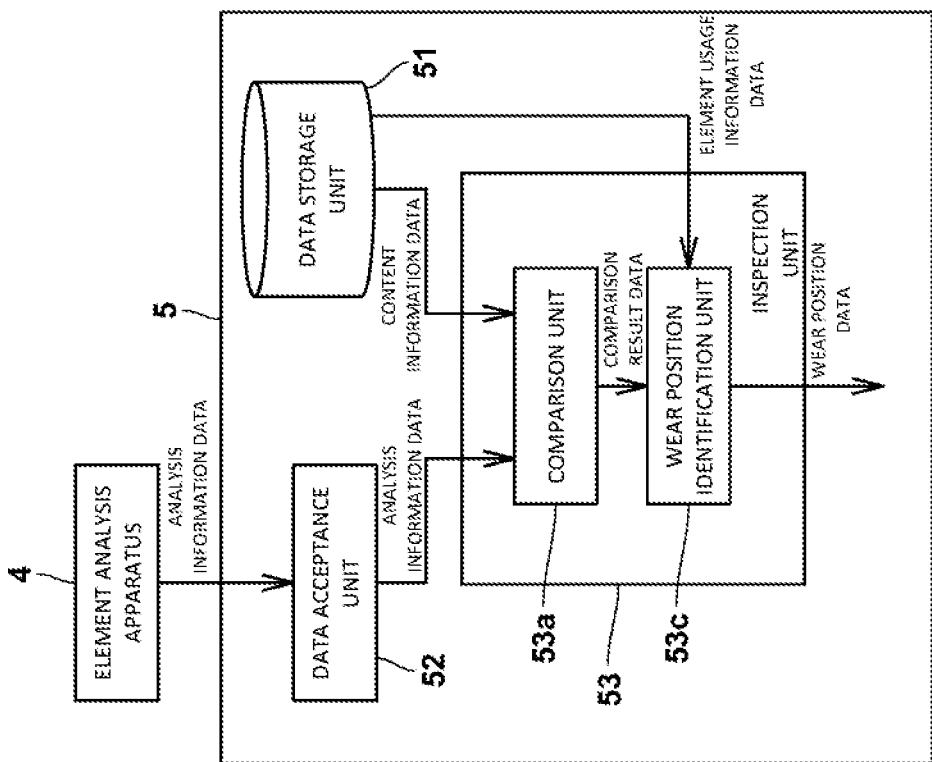
FIG. 5 is a schematic diagram illustrating a functional configuration of an inspection apparatus according to a second embodiment.

Specifically, the inspection apparatus 5 acquires data indicating an analysis result acquired by the element analysis apparatus 4 to identify the wear position in the engine E. The inspection apparatus 5 is a dedicated or general-purpose computer including a CPU, an internal memory, an input/output interface, and an AD converter. The CPU and other constituents in the inspection apparatus 5 cooperate based on an inspection program stored in the internal memory, thereby performing functions of the data storage unit 51, the data acceptance unit 52, the inspection unit 53 (the comparison unit 53a and a wear position identification unit 53c) as shown in FIG. 5. Each of the units will be described below.

The data storage unit 51 stores content information about the plurality of elements contained in the engine oil and usage information about the plurality of elements used in each unit of the engine E. The content information and the usage information is digital data. The content information may include known concentration (for example, the mass concentration or the element concentration) on the plurality of elements contained in the engine oil as well as the composition ratio of the plurality of elements. In the usage information, the components of the engine are associated with compositions of materials for the components. The content information and the usage information may be previously inputted by the user, or may be transmitted from the server via the Internet.

The data acceptance unit 52 accepts digital data indicating the analysis information acquired by the element analysis apparatus 4. The analysis information may include the measured concentration (for example, the mass concentration) of the plurality of elements contained in the engine oil as well as the composition ratio of the plurality of elements. Then, the data acceptance unit 52 transmits digital data indicating the accepted analysis information to the inspection unit 53.

The inspection unit 53 compares the analysis information accepted by the data acceptance unit 52 with the content information stored in the data storage unit 51 to identify the wear position of the engine, in particular, functions as the comparison unit 53a and the wear position identification unit 53c.

The comparison unit 53a acquires the analysis information and the content information, and compares the ratios (proportions) of the plurality of elements in the engine oil with the ratios (proportions) of the plurality of elements in the exhaust gas. Then, the comparison unit 53a identifies the element having a difference between the both ratios (proportions) outside the predetermined range. The predetermined range described herein is the range that can appropriately identify the ratios of the plurality of elements in the engine oil. In the case where an element that is not contained in the engine oil is contained in the exhaust gas, the element is identified as the element outside the predetermined range.

It is assumed that the ratios of the plurality of elements in the engine oil is P:1, S:2, Ca:1, Ze:5, Mo:1. In this case, when the ratios of the plurality of elements in the exhaust gas are P:1, S:2, Ca:1, Ze:5, Mo:1, Fe:1, the comparison unit 53a identifies Fe as the element outside the redetermined range. When the ratios of the elements of Cu:1, Sn:6, Si:1.5 are measured, it may be determined as a material for a metallic slide bearing. When a plurality of predetermined elements are detected with predetermined ratios, a wear site can be identified.

The wear position identification unit 53c detects an element identified as being out of the predetermined range by the comparison unit 53a, as a wear element generated by wearing. In the case where the element out of the range is not included in the plurality of elements in the usage information, the wear position identification unit 53c excludes the element out of the range from the wear element. Then, the wear position identification unit 53c identifies the wear position of the engine E based on the usage information and the wear element.

Advantageous Effect of Second Embodiment

The engine oil consumption measurement apparatus 100 according to the second embodiment may compare the plurality of elements in the engine oil with the plurality of elements in the exhaust gas, to detect the wear element generated by the wearing of the engine E. Here, if the usage information about the elements of each component of the engine E are given, the wear position can be identified based on the wear element.

The present invention is not limited to the above-mentioned embodiments.

The exhaust gas may contain elements derived from the fuel for the engine E in addition to elements derived from the engine oil. The elements derived from the engine E may contribute to a measurement error of the engine oil consumption. For this reason, in each of the above embodiments, the data storage unit 51 may further store content information about a plurality of elements in the fuel for engine E, and the inspection unit 53 may compare the content information about the engine oil and the content information about the fuel with the analysis information to calculate the engine oil consumption or the wear element. For example, the quantity of the elements derived from the fuel in the analysis information may be subtracted from the fuel consumption and the fuel content information, or the element analysis apparatus 4 may measure the quantity of the elements contained only in the fuel, and the measured quantity of the elements derived from the fuel may be subtracted from the analysis information. Using the analysis information after the subtraction, the engine oil consumption is calculated, or the wear element is detected as in the embodiments.

The element analysis apparatus in the embodiments uses the fluorescent X-ray analyzing instrument and however, may be an element analysis apparatus using other measuring principles. Any element analysis apparatus that can quantitatively analyze the discharged mass of the elements collected by the filter may measure the engine oil consumption using the discharged mass and the content information. Similarly, the wear position may be identified using the discharged mass, the content information, and the usage information.

Further, according to the embodiments, the filter collects the PM particles to analyze the elements and however, an analyzer for analyzing a plurality of elements may be provided in an exhaust gas path to measure the plurality of elements. Analysis information acquired by the analyzer is inputted to the inspection apparatus 5.

Moreover, the inspection apparatus may perform background correction. That is, the engine oil consumption may be calculated, or the wear element may be detected by detecting elements contained in air sucked into the engine, and subtracting the air-derived elements.

In addition, the inspection apparatus may have an exhaust gas analysis apparatus for measuring the concentration of an ingredient to be measured, such as $CO_2$, in the exhaust gas, and associate the concentration of the target ingredient, which is acquired by the exhaust gas analysis apparatus, with the detection state of engine oil consumption or the wear element and then to manage the association as data. The state of the engine or the engine oil may be checked based on the association.

According to each of the above-mentioned embodiments, in the case of using the filter 3 of winding type with the feed roll and the winding roll, information indicating the operating state of the engine or the like may be printed on the filter 3. This facilitates processing, use, or management of data.

The inspection apparatus according to the second embodiment compares the content information about the engine oil with the analysis information acquired by the element analysis apparatus to inspect the internal state of the engine (the worn member and the wear position) and however, may be configured as follows. That is, the inspection apparatus may include the data storage unit that stores content information (for example, the constituent ratio of constituent elements) about the elements contained in materials for the components of the engine, the data acceptance unit that accepts analysis information about the plurality of elements contained in the exhaust gas from the element analysis apparatus, and the inspection unit that compares the content information about the materials for the components with the analysis information to identify the worn member or the wear position of the engine.

Various modifications and combinations of the embodiments may be made within the scope of the subject matter of the present invention.

REFERENCE SIGNS LIST

100 Inspection system
E Engine
2 Sampling apparatus
3 Filter
4 Element analysis apparatus
5 Inspection apparatus
51 Data storage unit
52 Data acceptance unit
53 Inspection unit

The invention claimed is:

1. An inspection apparatus for inspecting an engine oil consumption of an engine including engine oil by using an exhaust gas of the engine, the inspection apparatus comprising:
    memory configured to store content information including ratios of a plurality of elements contained in the engine oil; and
    a processor programmed to
        accept analysis information including ratios of a plurality of elements contained in the exhaust gas,
        obtain from the memory the ratios of the plurality of elements contained in the engine oil,
        compare the ratios of the plurality of elements in the engine oil with the ratios of the plurality of elements in the exhaust gas,
        identify elements of the plurality of elements having a difference, within a predetermined range, between the ratios of the plurality of elements in the engine oil and the ratios of the plurality of elements in the exhaust gas, and
        calculate a value of the engine oil consumption using the elements having the difference within the predetermined range such that the value is more accurate than a measure of the engine oil consumption obtained using a single element of the engine oil, wherein the predetermined range is a range for identifying the plurality of the elements in the engine oil.

2. The inspection apparatus according to claim 1, wherein the memory is further configured to store content information about a plurality of elements contained in a fuel for the engine, and
the processor is further programmed to compare the content information about the engine oil with the content information about the fuel with the analysis information to calculate the engine oil consumption.

3. The inspection apparatus according to claim 1, wherein the inspection unit inspects wearing of the engine as the internal state of the engine.

4. The inspection apparatus according to claim 3, wherein the inspection unit compares ratios of the plurality of elements in the engine oil with ratios of the plurality of elements in the exhaust gas, and detects the element having a difference between the both ratios out of a predetermined range as a wear element by wearing.

5. The inspection apparatus according to claim 4, wherein the data storage unit further stores usage information about a plurality of elements used in each component of the engine, and
the inspection unit identifies a wear position in the engine based on the usage information and the wear element.

6. An inspection system comprising:
the inspection apparatus according to claim 1;
a filter that collects ingredients contained in an exhaust gas of an engine; and
an element analysis apparatus configured to analyze elements in the ingredients collected by the filter and generate the analysis information.

7. The inspection apparatus according to claim 1, wherein the processor is further programmed to calculate the value of the engine oil consumption by averaging a calculated engine oil consumption of each of the elements having the difference within the predetermined range.

* * * * *